United States Patent

Buch-Rasmussen et al.

(10) Patent No.: US 6,485,453 B1
(45) Date of Patent: Nov. 26, 2002

(54) CASSETTE FOR STORING AND INSERTION OF SOLID MEDICINE

(75) Inventors: Thomas Buch-Rasmussen, Gentofte (DK); Søren Aasmul, Holte (DK); James M. Flink, Frederiksberg (DK); Philip Hansen, Holte (DK); Claus Juul-Mortensen, Frederiksberg (DK); Jens Ulrik Poulsen, Virum (DK)

(73) Assignee: Novo Nordisk A/S, Bagsvaard (DK)

( * ) Notice: Subject to any disclaimer, the term of this patent is extended or adjusted under 35 U.S.C. 154(b) by 0 days.

(21) Appl. No.: 09/548,957

(22) Filed: Apr. 13, 2000

Related U.S. Application Data

(60) Provisional application No. 60/130,625, filed on Apr. 22, 1999.

(30) Foreign Application Priority Data

Apr. 16, 1999 (DK) ........................................ 1999 00509

(51) Int. Cl.[7] .............................................. A61M 31/00
(52) U.S. Cl. .......................................... 604/57; 604/59
(58) Field of Search ........................ 604/57, 59, 60–64, 604/285–288, 309, 11, 14, 15; 600/7–8; 222/144, 145.4, 162, 167–172; 206/363–367

(56) References Cited

U.S. PATENT DOCUMENTS

| | | | |
|---|---|---|---|
| 3,072,121 A | 1/1963 | Feldmann | 128/217 |
| 4,077,406 A | 3/1978 | Sandhage et al. | 128/217 |
| 4,451,254 A | 5/1984 | Dinius et al. | 604/62 |
| 4,576,591 A | 3/1986 | Kaye et al. | 604/62 |
| 4,915,686 A * | 4/1990 | Frederick | 604/60 |
| 4,946,035 A | 8/1990 | Grimm et al. | 206/366 |
| 5,021,241 A | 6/1991 | Yamahira et al. | 424/426 |

FOREIGN PATENT DOCUMENTS

| | | |
|---|---|---|
| WO | WO 93/23110 | 11/1993 |
| WO | WO 94/22423 | 10/1994 |
| WO | WO 96/08289 | 3/1996 |

* cited by examiner

*Primary Examiner*—Anhtuan T. Nguyen
*Assistant Examiner*—Catherine Serke
(74) *Attorney, Agent, or Firm*—Marc A Began, Esq.; Reza Green; Richard Bork

(57) ABSTRACT

A cassette for storing and insertion of a solid medicine peg appears as a unit having a first bore (2) which accommodates the medicine peg (3) and has a diameter corresponding to the diameter of this peg (3), a second bore (4) in coaxial extension of the first bore (2) and having a diameter larger than the diameter of the first bore (2), an inserter having a shaft (5) fitting into the first bore (2) and a guiding head (6) in coaxial extension of the shaft (5) fitting into the second bore. The inserter shaft (5) has one end adjacent to the peg (3) and the other connected to the guiding head (6) which projects from the cassette. The head (6) fits into the second bore with a fitting providing a diffusion tight sealing and the distal end of the unit is closed by a membrane diffusion tightly sealing this distal end.

11 Claims, 1 Drawing Sheet

CASSETTE FOR STORING AND INSERTION OF SOLID MEDICINE

CROSS-REFERENCE TO RELATED APPLICATIONS

This application claims priority under 35 U.S.C. 119 of Danish application PA 1999 00509 filed on Apr. 16, 1999, and U.S. application No. 60/130,625 filed on Apr. 22, 1999, the contents of which are fully incorporated herein by reference.

BACKGROUND OF THE INVENTION

Many types of medicine are given as solutions or suspensions of a medical active substance which are subcutaneously or intramuscularly administered.

Many advantages are obtained if the solid medicine, instead of being dissolved or suspended, is formed as small needle shaped pegs which are inserted directly into the tissue where they are dissolved in the tissue fluids and in this way administered in the body. Such pegs can be given a size which is comparable to the size of the needle which is used for the injection of the corresponding fluid medicine. As the medicine itself is the needle, no used needles need to be disposed of after the insertion and consequently the risk of accidental needle scratches is eliminated. Further, most medicine has a longer shelf life in a solid state than in a solution.

A problem with the solid medicament pegs is their size. As they have to be sufficiently thin to be comparable with an injection needle, their thickness is about 1 mm or less. And, to ensure a deposition in the subcutaneous layer of the skin, they have to be short, preferably in the interval 1–10 mm. Such sizes can hardly be handled without a tool such as a pincer and even with a pincer the handling is difficult especially for sight impaired people.

It is an object of the invention to provide means for storage and insertion of solid medicine pegs.

From WO 96/08289 is known a disposable device loaded with one medicine peg which can be inserted into the skin by the device. Whereas such a device is acceptable for the insertion of pegs of a medicament which shall be taken once in a while, it is less convenient for medicaments such as insulin which shall be taken frequently as the user has to bring with him a number of devices corresponding to the number of doses he is going to take during the time he is away from his home. Diabetics will prefer a device by which single pegs can be inserted from a cassette in which a number of such pegs are stored.

WO 96/08289 also describes a device which by pressurized air accelerates the peg from a cassette through a barrel to shoot it into the skin. As it is important for diabetics that the medicament is inserted subcutaneously, a device by which the peg is by a plunger followed to its subcutaneous position is preferred as being more precise than a shooting device.

Further, in the device according to WO 96/08289 no attention has been paid to the fact that the medicament is biodegradable and has to be kept absolutely dry until it is implanted, i.e., the implant has to be stored in a vessel which is diffusion tightly sealed.

BRIEF DESCRIPTION OF THE INVENTION

Instead of the device in WO 96/08289 by which the user presses the peg through the skin, a device is preferred by which the medicine implant is moved to its subcutaneous position by an impact. Such a device may comprise a socket for a cassette with medicine pegs and a hammer which can, against the force of a spring, be brought to a cocked position from which it can be released to return and hit an anvil from which the impact is transmitted to the medicine peg.

An object of the invention is to provide a cassette loaded with pegs for use in such an insertion device.

A cassette for storing and insertion of solid medicine is according to the invention characterised in that it comprises at least one unit having a first bore accommodating a medicine peg and having a diameter corresponding to the diameter of this peg, a second bore in coaxial extension of the first bore and having a diameter larger than the diameter of the first bore, an inserter comprising an inserter shaft which fits into the first bore and a guiding head connected to the inserter shaft in coaxial extension of this inserter shaft and fitting into the second bore, the inserter shaft having a distal end adjacent to a proximal end of the peg and a proximal end connected to a distal end of the guiding head, which guiding head forms at its proximal end an anvil, the second bore having a length so that the distal end of the inserter shaft is moved to a position extending over the distal end of the housing a distance corresponding to a wanted insertion depth for the when the distal end of the guiding head is moved to the bottom of the second bore.

As the shaft is very thin it is important that the impact force which is transmitted through this shaft is strictly axial as a skew force may cause the shaft to bend. The guiding head sliding through the second bore will compensate a possible skew impact on the anvil end of the guiding head so that only an axial force is transmitted to the shaft. The shaft must only have a length corresponding to the distance which the peg has to be moved to be passed from its position in the first bore to its position in the tissue in which it is inserted. Keeping the shaft as short as possible further minimises the risk for bending.

According to the invention the medicine peg may be moulded in the first bore. This way handling of the small peg is made easier and it is guarantied that the diameter of the peg corresponds to the inner diameter of said first bore.

The head of the inserter may fit into the second bore with a fitting making the head provide a diffusion tight sealing of the proximal end of the second bore, and the distal end of the first bore may be closed by a membrane diffusion tightly sealing the distal end of the unit. This enables a sterile storage of the individual pegs until they are inserted. The membrane is weakened to make it burst in a controlled way not to leave debris of the membrane when the peg is forced through it.

The membrane may be formed integral with the material of the cassette or it may be applied as a separate member, e. g. a metal foil covering the opening of the distal end of the first bore, or it may be embedded in the cassette material adjacent to the distal end of the first bore.

To ease the mounting of an inserter in a unit the transition from the second bore to the first bore may be made funnel shaped.

The guiding head of the inserter may appropriately have a length ensuring that the anvil end of this guiding head projects from the proximal end of the cassette when an impact on the anvil has moved the peg to its wanted position in the skin of a user. As the proximal end of the peg must be placed a distance under the skin, the distal end of the shaft pushing the peg must be moved to a position in which it projects a corresponding distance from the distal end of the unit. The anvil end of the guiding head may be provided with a flange which can be engaged by a draw out mechanism in the not shown insertion device which draw out mechanism can after an insertion of a peg draw the inserter back to hide the distal end of the inserter shaft in the first bore when the peg stored in that bore has been inserted.

The drawing back of the inserter may be accomplished in other ways, e. g. by use of a coil spring surrounding the shaft between the distal end of the guiding head and the bottom of the second bore. Alternatively the compression of the air in the space between the distal end of the guiding head and the bottom of the second bore can be relied on as a means for moving backwards the inserter after it has by an impact on the anvil been moved in a distal direction to insert a peg.

In the cassette the array of units may form a beam, which can be moved by the insertion apparatus so that a new unit is moved to an insertion position each time the hammer mechanism has caused insertion of the peg in the unit which is at the moment placed in the insertion position.

The cassettes may be provided with guiding projections or indentions to ensure their correct guiding through and positioning in the insertion device

BRIEF DESCRIPTION OF THE DRAWINGS

In the following the invention is further described with references to the drawing, wherein.

DETAILED DESCRIPTION OF THE INVENTION

Figure 1:
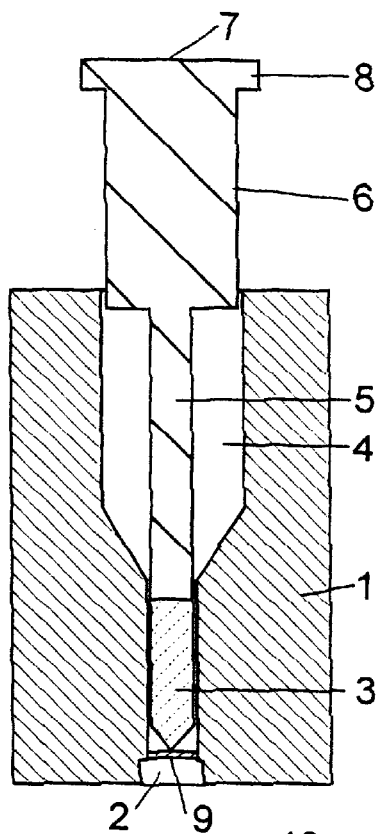
FIG. 1 shows schematically a sectional view through an insert unit.

The insert unit in FIG. 1 comprises a housing 1 with a first bore 2 having a diameter corresponding to the diameter of a peg positioned in said first bore 1 which opens through a first end of the housing. The peg 3 is made from the effective drug which shall be injected and which drug may be mixed with a bio-compatible binder to give the peg a sufficient strength to penetrate the skin without crushing. A second bore 4 in axial extension of the first bore 2 has a larger diameter than this first bore and opens through a second end of the housing 1. An inserter comprises an inserter shaft 5 having a diameter corresponding to the diameter of the peg 3, and a guiding head 6 having a diameter corresponding to the diameter of the second bore 4. The inserter shaft 5 and the inserter head 6 are connected to each other and lies in axial extension of each other. A free end of the inserter shaft 5 is inserted in the first bore 2 adjacent to the peg 3. The other end of the shaft 5 is coupled to the guiding head 6 and has a length which ensures that a part of the guiding head is inserted in the end of the second bore 4 opening through the second end of the housing 1. The length of the second bore 4 is so adapted that the free end of the inserter projects over the first end of the housing when the end of the guiding head inserted in the second bore 4 is moved to the bottom of this bore. The length of the guiding head is so adapted that its outer end still projects over the second end of the housing 1 when its inner end reaches the bottom of the second bore 4. The end surface of the outer end of the guiding head 6 forms an anvil 7, which can be impacted by a hammer mechanism in a not shown insert device. The outer end of the guiding head 6 is provided with a flange 8 which can be engaged by a withdraw mechanism in the not shown insert device to draw the inserter back from its position with the end of the inserter shaft 5 projecting from the first end of the housing 1.

In the shown embodiment of the inserter unit the transition zone between the first 2 and the second 4 bore is funnel shaped to ease the mounting of the inserter with the free end of its shaft guided in the first bore 2. The peg 3 is pointed at the end which shall penetrate the skin to make this penetration easier. The pointed end has the shape of a cone with a apex angle in the interval 30° to 90° preferably between 50°–70°. The end of the first bore 2 from which the peg 3 is pushed into the skin is closed by a membrane 9 which can be integral with the housing or be a metal foil embedded in the material of the housing. In the shown embodiment this membrane lies inside the first bore in a distance from the opening of this bore. Over this distance the first bore is given a slightly enlarged diameter to make room for flaps of the membrane, which are formed when the membrane 9 is penetrated by the peg 3.

Cassettes comprising more units can be shaped as beams, cylinders or bands which can be mounted in an insertion mechanism in which the cassette is advanced to place a unused unit in an insertion position in which a hammer can be released to hit the anvil of the unit in question to move the peg out of the housing into the skin. Before use the peg is stored sterilely in the housing, the bore through which the peg is delivered being covered by a diffusion tight membrane and the other end with the wider second bore being closed by the inserter head fitting with a press fitting into this second bore. For the insertion of medicaments of which only one dose is needed, so as glucagon, adrenaline or atropine, a single cassette may be used whereas implantation of medicaments, which have to be applied frequently, such as insulin or growth hormone, an array of more units is preferred. The units may be arrayed on line in a beam shaped cassette or in a revolver drum shaped cassette or a number of single cassettes may be designed to be hinged together to form a cartridge belt. The choice of design may depend on the number of units, which shall be arrayed.

Figure 2:
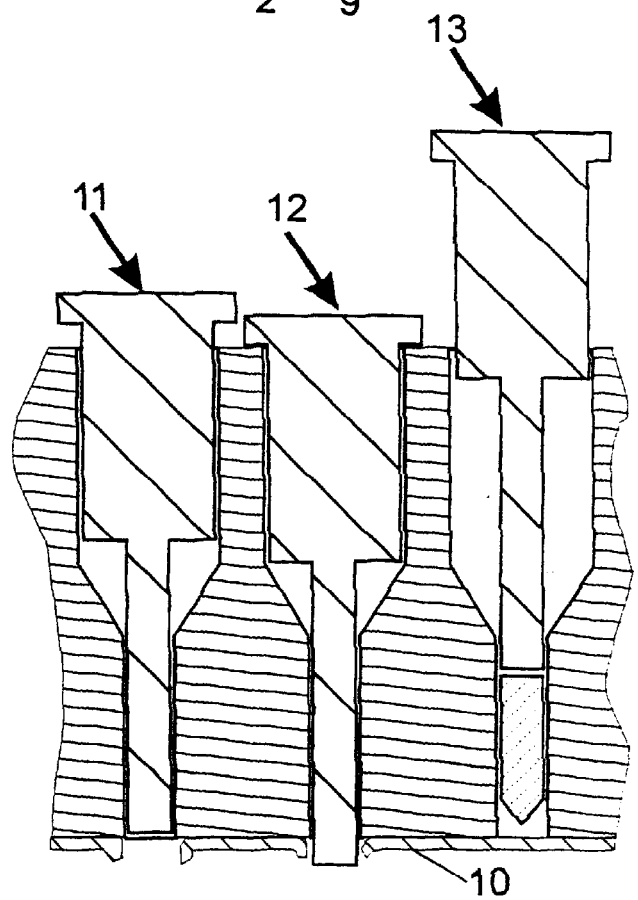
FIG. 2 shows a sectional view of a part of a beam shaped insert unit cassette with inserter units in different conditions.

FIG. 2 shows a part of a beam with three insertion units. The first unit 11 is shown in a position wherein the inserter is shown in the position it has after insertion of the peg and after the inserter is drawn back from its position with the end of the inseter shaft projecting over the first end of the housing. The unit 12 is shown in the position immediately after an impact on the anvil 7 in which position the end of the inserter shaft is still projecting from the first side of the housing. Finally the unit 13 is in the storing position where it has not yet been operated. The first end of the units 11, 12 and 13 are covered by a foil 10 which is sealed to the surface formed by the first ends of the integral housing of the units. The foil 10 may be made from metal, plastic of laminates of different types of plastic or of metal and plastic.

What is claimed is:

1. A cassette for storing and insertion of a solid medicine peg, said cassette comprising a housing at least one unit having a first bore (2) accommodating the medicine peg (3) and having a diameter corresponding to the diameter of the peg (3), a second bore (4) in coaxial extension of the first bore (2) and having a diameter larger than the diameter of the first bore (2), an inserter comprising an inserter shaft (5) fitting into the first bore (2) and a guiding head (6) connected to the inserter shaft (5) in coaxial extension of the inserter shaft and fitting into the second bore, the inserter shaft (5) having a distal end adjacent to a proximal end of the peg (3) and a proximal end connected to a distal end of the guiding head (6) which forms at its proximal end an anvil (7), the second bore (4) having a length so that the distal end of the inserter shaft (5) is moved to a position extending beyond the distal end of the housing a distance corresponding to a wanted insertion depth for the peg when the distal end of the guiding head is moved to a bottom of the second bore, wherein the head (6) of the inserter fits into the second bore with a press fitting which provides a diffusion tight sealing of the proximal end of the unit, and wherein the distal end of the unit is closed by a membrane diffusion tightly sealing the distal end of the unit.

2. A cassette according to claim 1, wherein the medicine peg is molded in the first bore.

3. A cassette for storing and insertion of a solid medicine peg, said cassette comprising a housing at least one unit having a first bore (2) accommodating the medicine peg (3) and having a diameter corresponding to the diameter of the peg (3), a second bore (4) in coaxial extension of the first bore (2) and having a diameter larger than the diameter of the first bore (2), an inserter comprising an inserter shaft (5) fitting into the first bore (2) and a guiding head (6) connected to the inserter shaft (5) in coaxial extension of the inserter shaft and fitting into the second bore, the inserter shaft (5) having a distal end adjacent to a proximal end of the peg (3) and a proximal end connected to a distal end of the guiding head (6) which forms at its proximal end an anvil (7), the second bore (4) having a length so that the distal end of the inserter shaft (5) is moved to a position extending beyond the distal end of the housing a distance corresponding to a wanted insertion depth for the peg when the distal end of the guiding head is moved to a bottom of the second bore, wherein the cassette comprises a number of integral units arrayed in a beam shaped housing.

4. A cassette for storing and insertion of a solid medicine peg, said cassette comprising a housing at least one unit having a first bore (2) accommodating the medicine peg (3) and having a diameter corresponding to the diameter of the peg (3), a second bore (4) in coaxial extension of the first bore (2) and having a diameter larger than the diameter of the first bore (2), an inserter comprising an inserter shaft (5) fitting into the first bore (2) and a guiding head (6) connected to the inserter shaft (5) in coaxial extension of the inserter shaft and fitting into the second bore, the inserter shaft (5) having a distal end adjacent to a proximal end of the peg (3) and a proximal end connected to a distal end of the guiding head (6) which forms at its proximal end an anvil (7), the second bore (4) having a length so that the distal end of the inserter shaft (5) is moved to a position extending beyond the distal end of the housing a distance corresponding to a wanted insertion depth for the peg when the distal end of the guiding head is moved to a bottom of the second bore, wherein the cassette comprises a number of integral units arrayed along the periphery of a drum.

5. A cassette for storing and insertion of a solid medicine peg, said cassette comprising a housing at least one unit having a first bore (2) accommodating the medicine peg (3) and having a diameter corresponding to the diameter of the peg (3), a second bore (4) in coaxial extension of the first bore (2) and having a diameter larger than the diameter of the first bore (2), an inserter comprising an inserter shaft (5) fitting into the first bore (2) and a guiding head (6) connected to the inserter shaft (5) in coaxial extension of the inserter shaft and fitting into the second bore, the inserter shaft (5) having a distal end adjacent to a proximal end of the peg (3) and a proximal end connected to a distal end of the guiding head (6) which forms at its proximal end an anvil (7), the second bore (4) having a length so that the distal end of the inserter shaft (5) is moved to a position extending beyond the distal end of the housing a distance corresponding to a wanted insertion depth for the peg when the distal end of the guiding head is moved to a bottom of the second bore, wherein the cassette comprises a number of single unit cassettes hinged together to form a cartridge band.

6. A cassette according to claim 1, wherein the cassette comprises a number of integral units arrayed in a beam shaped housing.

7. A cassette according to claim 2, wherein the cassette comprises a number of integral units arrayed in a beam shaped housing.

8. A cassette according to claim 1, wherein the cassette comprises a number of integral units arrayed along the periphery of a drum.

9. A cassette according to claim 2, wherein the cassette comprises a number of integral units arrayed along the periphery of a drum.

10. A cassette according to claim 1, wherein the cassette comprises a number of single unit cassettes hinged together for form a cartridge band.

11. A cassette according to claim 2, wherein the cassette comprises a number of single unit cassettes hinged together for form a cartridge band.

\* \* \* \* \*

UNITED STATES PATENT AND TRADEMARK OFFICE
CERTIFICATE OF CORRECTION

PATENT NO. : 6,485,453 B1
APPLICATION NO. : 09/548957
DATED : November 26, 2002
INVENTOR(S) : Buch-Rasmussen et al.

Page 1 of 1

It is certified that error appears in the above-identified patent and that said Letters Patent is hereby corrected as shown below:

Claim 1

Column 4, Line 53

Delete "a housing" after the word comprising

Claim 3

Column 5, Line 11

Delete "a housing" after the word comprising

Claim 4

Column 5, Line 31

Delete "a housing" after the word comprising

Claim 5

Column 6, Line 6

Delete "a housing" after the word comprising

Signed and Sealed this

First Day of July, 2008

JON W. DUDAS
*Director of the United States Patent and Trademark Office*